United States Patent [19]

Fukushima

[11] Patent Number: 4,607,641

[45] Date of Patent: Aug. 26, 1986

[54] ELECTRONIC SPHYGMOMANOMETER

[75] Inventor: Toshitaka Fukushima, Tokyo, Japan

[73] Assignee: Seiko Instruments & Electronics Ltd., Tokyo, Japan

[21] Appl. No.: 665,775

[22] Filed: Oct. 29, 1984

[30] Foreign Application Priority Data

| Nov. 4, 1983 [JP] | Japan | 58-207077 |
| Nov. 4, 1983 [JP] | Japan | 58-207078 |
| Nov. 4, 1983 [JP] | Japan | 58-207083 |
| Nov. 4, 1983 [JP] | Japan | 58-207084 |
| Nov. 9, 1983 [JP] | Japan | 58-210306 |
| Nov. 10, 1983 [JP] | Japan | 58-211654 |
| Apr. 20, 1984 [JP] | Japan | 59-80973 |

[51] Int. Cl.[4] .............................................. A61B 5/02
[52] U.S. Cl. .................................................. 128/680
[58] Field of Search .............................. 128/680–683; 364/415–417

[56] References Cited

U.S. PATENT DOCUMENTS 4,181,134  1/1980  Mason et al. ............... 128/690 X
4,261,368  4/1981  Danna et al. ............... 128/680

Primary Examiner—Kyle L. Howell
Assistant Examiner—Francis J. Jaworski
Attorney, Agent, or Firm—Robert E. Burns; Emmanuel J. Lobato; Bruce L. Adams

[57] ABSTRACT

An electronic sphygmomanometer comprises a detection section formed with an analog circuit and includes a detection circuit for detecting Korotkoff sounds, a pressure transducer for converting a pressure to an electric signal, and an analog section of analog to digital converter on one bipolar IC chip, a logical section formed with a digital circuit and including a digital section of analog to digital converter, an arithmetic unit and a display device for indicating systolic and diastolic pressure on the other MOS IC chip, and a plurality of signal lines connected between the detection section and the logic section so that the sphygmomanometer is attained to be small and low voltage and current driver type.

5 Claims, 11 Drawing Figures

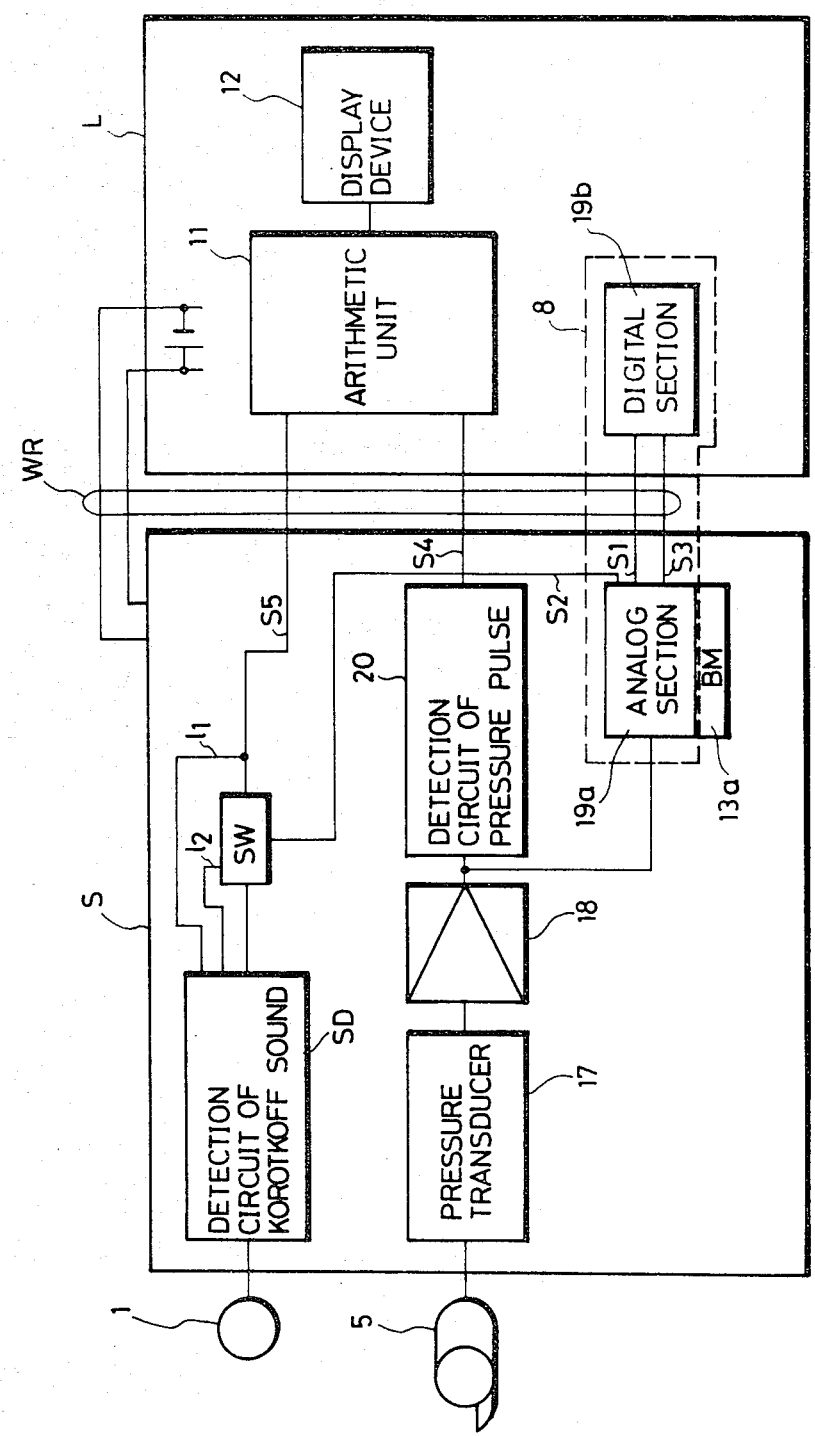

SYSTOLIC PRESSURE SIDE        DIASTOLIC PRESSURE SIDE

ID

ELECTRONIC SPHYGMOMANOMETER

BACKGROUND OF THE INVENTION

This invention relates to a small-size electronic sphygmomanometer.

The electronic sphygmomanometer includes an analog circuit and logic circuit.

In the analog circuit, which includes transistors, all the transistors operate in the active condition and dissipate high power.

Particularly, a semiconductive pressure transducer is required to operate by flowing relatively large current because the sensitivity of the transducer is proportional to the current value applied to it.

An operational amplifier is used in a pressure detection section and the elements used in the operational amplifier must be selected in view of offset voltage and temperature drift.

Further, external noise has to be considered in the case of amplification of alternating current.

On the other hand, it is advantageous that the logic circuit be operated in a saturation condition.

Accordingly, the logic circuit is capable of being formed as a C-MOS circuit fabricated on one chip.

Referring again to the analog circuit, the analog circuit includes a large number of resistors and capacitors in addition to bipolar transistors.

It is difficult for a small-size sphygmomanometer to be driven with low voltage and current because the desired amplitude of the signal voltage cannot be obtained using low voltage and current.

DESCRIPTION OF PRIOR ART

FIG. 1 is a circuit block diagram showing a general electronic sphygmomanometer and FIG. 2 is a graph showing the measurement principle of blood pressure.

A cuff 5 is wrapped about the upper arm of a person whose blood pressure is to be measured and the cuff is inflated to a pressure greater than the systolic pressure and then the pressure is decreased gradually.

In the process of decreasing the pressure, Korotkoff sounds (called K-sounds hereinafter) produced in the artery.

Upon further decreasing the pressure, the K-sounds disappear.

The pressure value at a time when the K-sounds are produced is defined as the systolic pressure and the pressure value at a time when the K-sounds disappear is defined as the diastolic pressure.

K-sounds are detected by a K-sound microphone 1 and are discriminated from noise by an amplifier 2 and a filter 3.

The analog output signal of the filter 3 is converted to a pulse signal by a comparator 4.

On the other hand, the pressure of the cuff 5 is converted to a voltage signal by a pressure transducer 6 and the converted voltage is amplified by an amplifier 7.

Then, the amplified voltage is read into an arithmetic unit 11 through an analog to digital converter 8.

The pressure of the cuff 5 is varied somewhat by the pulse pressure during the production of the K-sound.

Such variation is distinguished by a filter 9, and a comparator 10 produces a reference pulse at its output terminal and applies the reference pulse to the arithmetic unit 11.

The judgment of K-sound existence is conducted based on the reference pulse so that the measuring accuracy of the blood pressure is improved.

The arithmetic unit 11 determines the systolic and diastolic pressures and a display device 12 displays the systolic and diastolic pressure.

The reference numeral 13 depicts a battery monitoring circuit which detects the drop of the battery voltage.

SUMMARY OF THE INVENTION

It is an object of this invention to provide a small-size electronic sphygmomanometer using C-MOS logic IC and bipolar analog IC and which can operate using low voltage and current.

It is another object of this invention to provide an electronic sphygmomanometer in which an analog circuit section and a logic circuit section are separately formed, and in which an analog to digital converter for measuring blood pressure is comprised of an analog section and digital section.

It is another object of this invention to provide an electronic sphygmomanometer having a constant current circuit for driving a semiconductive pressure transducer and a double integral (dual-slope) type integrator serving as the analog to digital converter in which the variation of the pressure sensitivity produced by the current variation of the constant current is compensated by the double integral type integrator.

It is another object of this invention to provide an electronic sphygmomanometer in which a detection circuit for detecting the Korotkoff sound is improved to produce greater pulses as compared with the input pulses for Korotkoff sound.

It is another object of this invention to provide an electronic sphygmomanometer having an analog circuit section serving as transmitter, a logic circuit section serving as a receiver, and a signal line connected between the analog circuit section and the logic circuit section in which the signal line is used a as bidirectional line.

BRIEF DESCRIPTION OF THE DRAWINGS

FIG. 3 is a circuit block diagram showing one embodiment of this invention.

PREFERRED EMBODIMENT OF THE INVENTION

Figure 1:
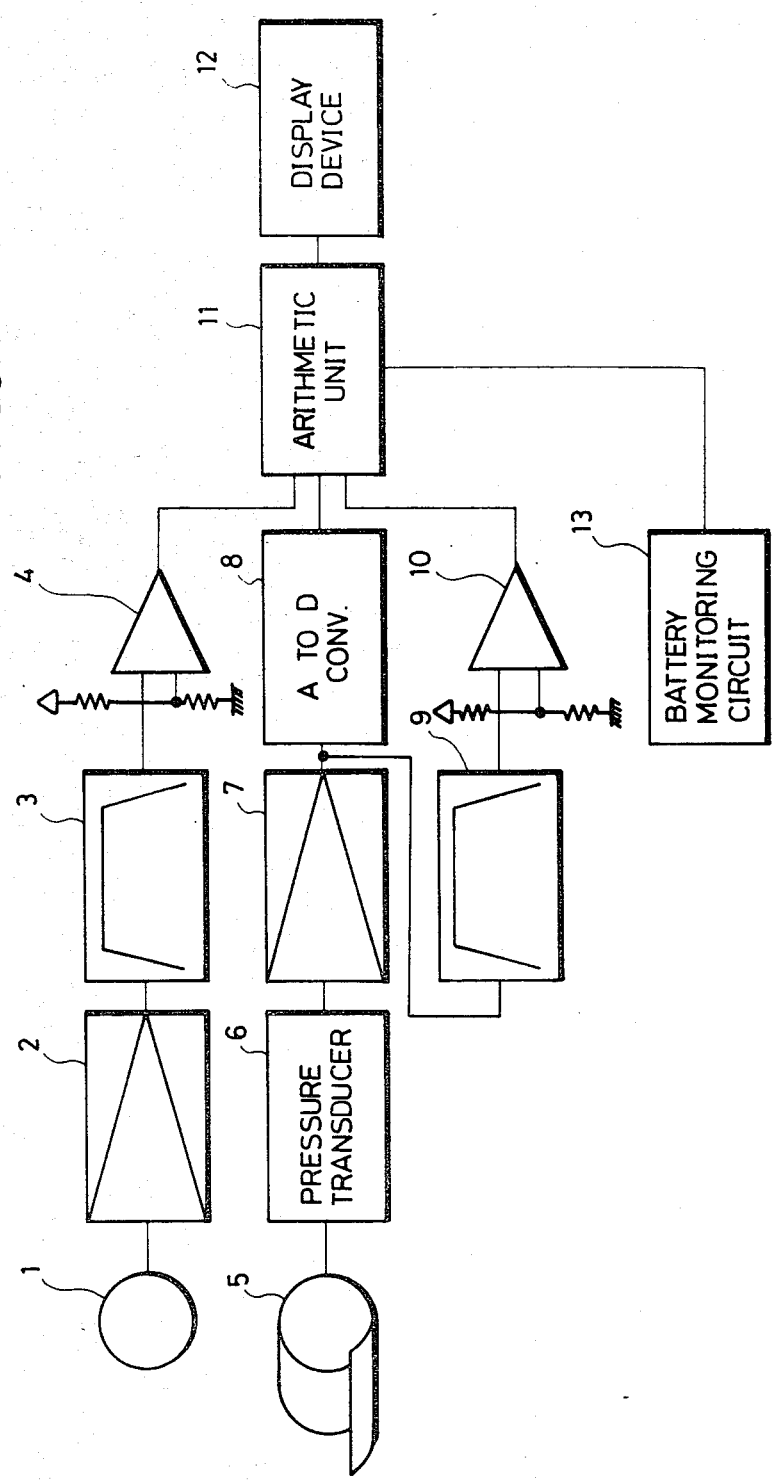
FIG. 1 is a circuit diagram showing the general construction of a conventional electronic sphygmomanometer.
Figure 2:
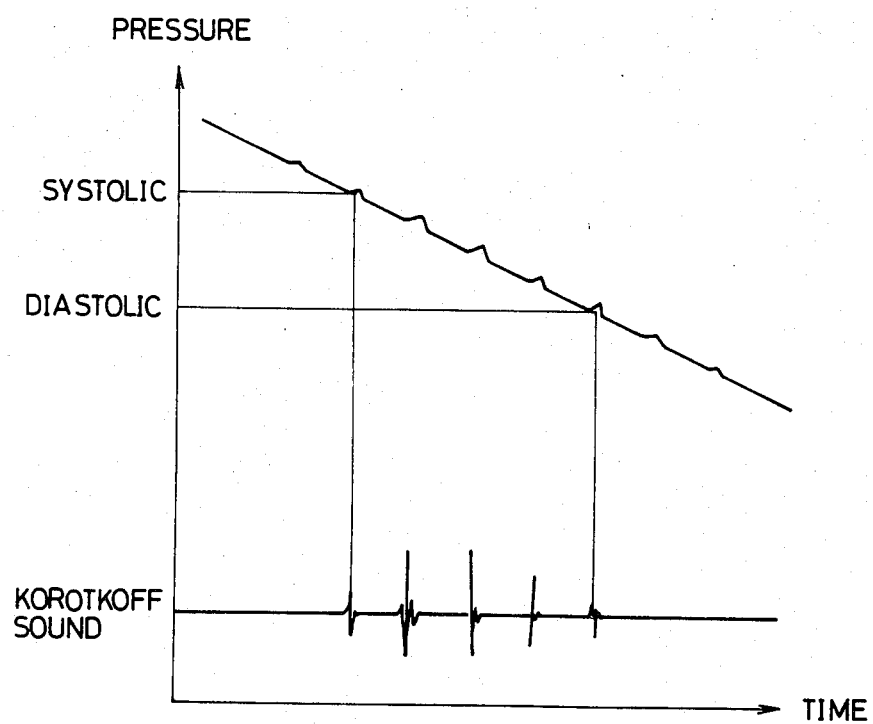
FIG. 2 is a graph showing the measurement principle of blood pressure.

FIG. 3 is a circuit block diagram showing one embodiment of this invention.

The circuit block diagram of the sphygmomanometer consists of an analog circuit serving as a detection section S, a digital circuit serving as a logic section L, a signal line section WR connected between the detection section S and the logic section L, and the microphone 1 and the cuff 5 connected to the detection section S.

The detection section S includes a detection circuit SD of Korotkoff sound, a pressure transducer 17, an amplifier 18, a detection circuit 20 of pressure pulse and an analog section 19a of an analog to digital converter 8.

The logic section L includes the arithmetic unit 11, a digital section 19b of the analog to digital converter 8 and the display device 12.

The analog detection section S is formed on a bipolar IC chip and the digital logic section L is formed on C-MOS IC chip.

The signal line section WR includes a signal line S5 connected through a switch circuit SW for using the signal line 5 as a bidirectional line between the detection circuit SD and the arithmetic unit 11, a signal line S4 connected between the detection circuit 20 of pressure pulse and the arithmetic unit 11, and signal lines S1 and S3 connected between the analog section 19a and the digital section 19b.

Herein, the detection section S is used as a transmitter, whereas the logic section L is used as a receiver.

Figure 4A:
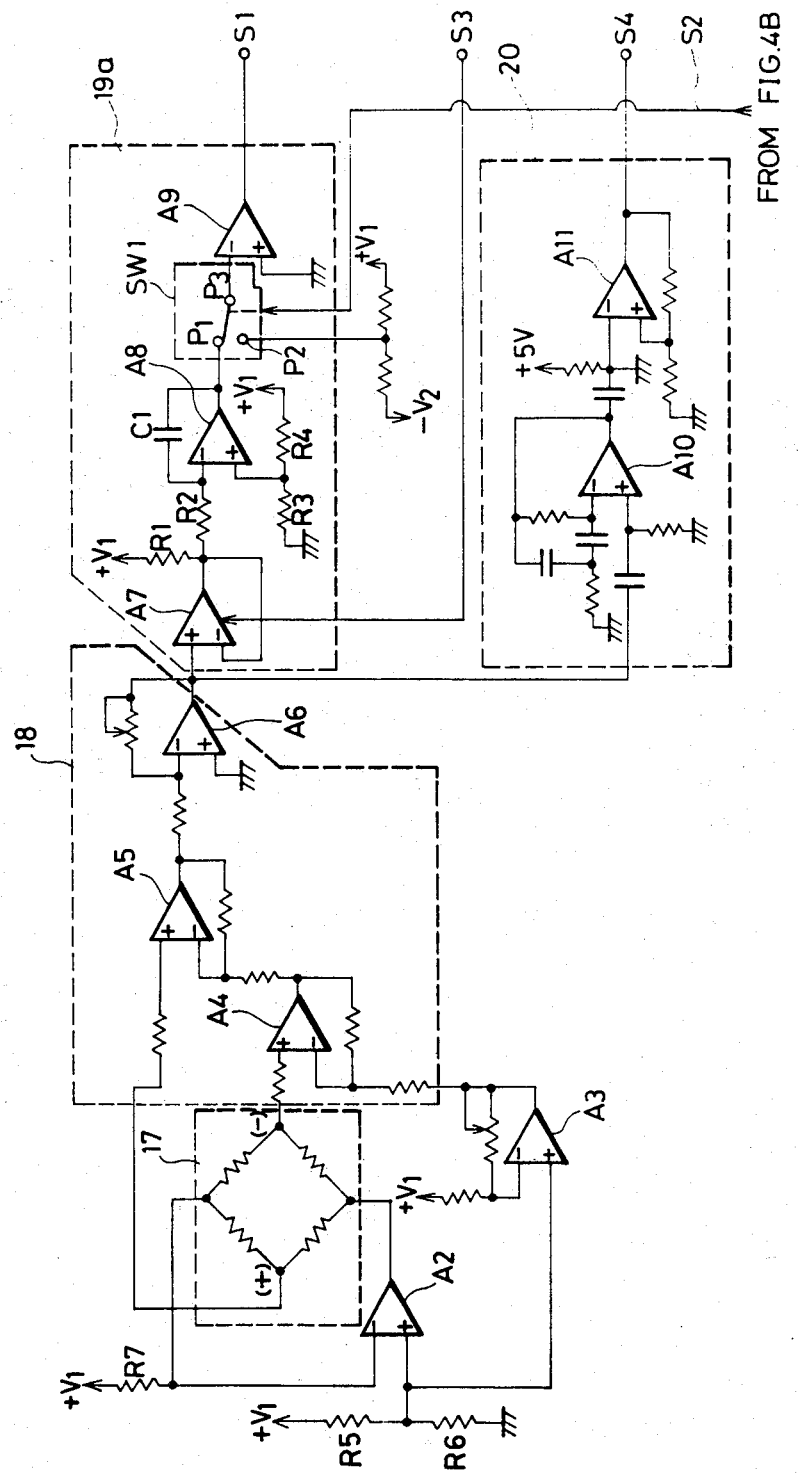
FIG. 4A is a circuit diagram showing a portion of a detection section used in this invention.
Figure 4B:
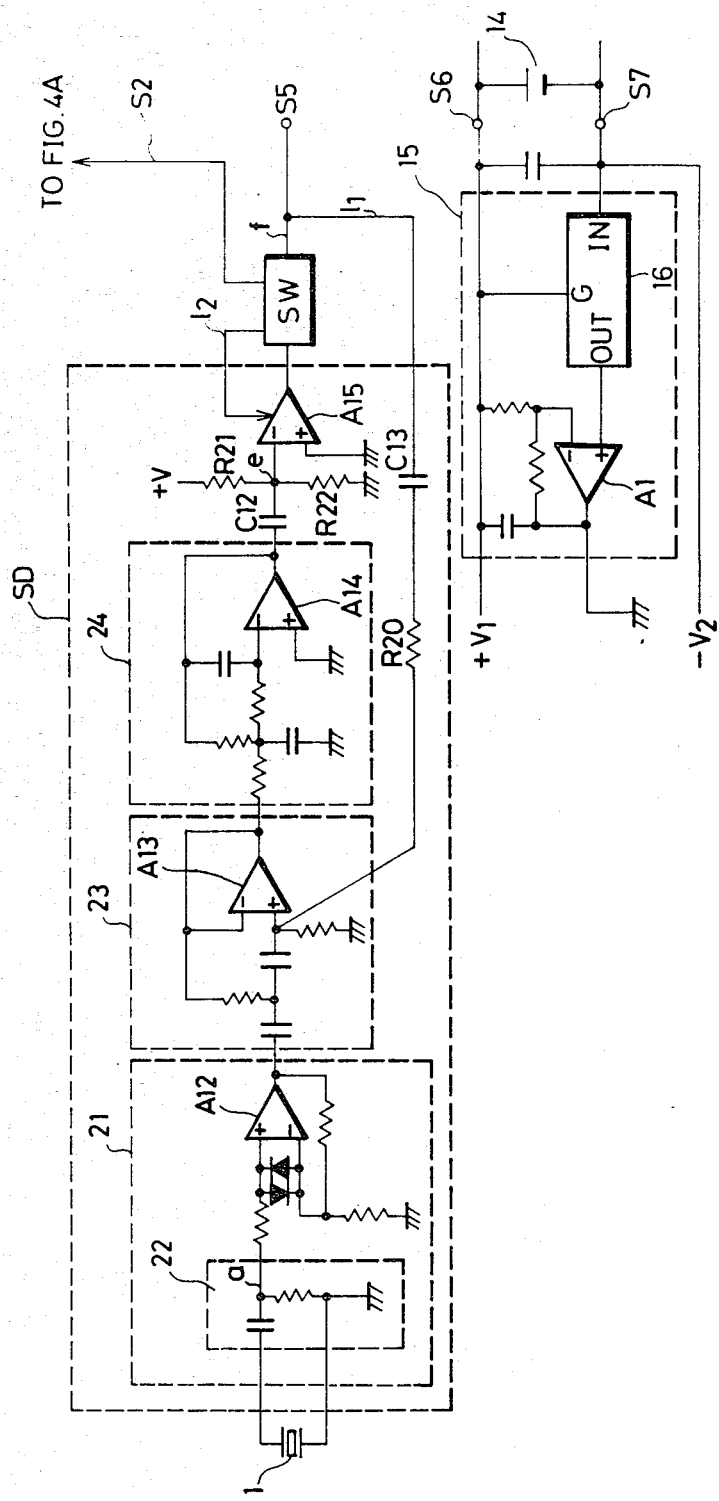
FIG. 4B is a circuit diagram showing another portion of the detection section.

FIGS. 4A and 4B show a circuit diagram of the detection section S of the sphygmomanometer.

The detection section S is constructed with bipolar transistors, which are actuated by about 3 volts.

In FIG. 4B, the reference voltage circuit 15 produces 1.2 volts at its output terminals.

The positive terminal of a battery 14 is of 1.2 volts (called $+V1$ hereinafter) and the negative terminal of the battery is of unstable voltage (called the negative terminal voltage $-V2$, hereinafter).

A reference voltage circuit 15 is comprised of a band gap reference circuit 16 and an operational amplifier A1.

The band gap reference circuit 16 produces a voltage using the energy gap of a semiconductor element and the voltage is lower by 0.6 volts as compared with $+V1$.

The reference voltage is produced by the amplifier A1 which amplifies the voltage produced by the band gap reference circuit 16. Referring next to the semiconductive pressure transducer 17, it is driven with constant current by an operational amplifier A2.

The constant current value is $+V1 \cdot R5/(R5+R6) \cdot R7$, the driving current is proportional to the sensitivity of the pressure, and the resistances of the pressure transducer are related to the sensitivity of the pressure to be measured.

The amplifier 18 includes low offset type operational amplifiers A4–A6, and an amplifier A3 is used for adjusting the offset voltage.

The signal output of the amplifier 18 is applied to the analog section 19a of the analog to digital converter 8 and to the detection circuit 20 for detecting the pressure pulse.

The analog section 19a of the analog to digital converter 8 comprises a double integral type integrator, and it is charged while the signal line S3 is in the high level and discharged at constant current while the signal line S3 is in the low level.

Referring next to the analog section 19a of the double integral type integrator, an operational amplifier A7 functions as a voltage-follower when the signal line S3 is in the high level.

The signal voltage of the amplifier 18 has the same polarity as that of "V2" and the charge current of the amplifier 18 is determined by the resistor R2.

In this state, a resistor R1 determines the bias current of the output stage of the operational amplifier A7.

The operational amplifier A7 is completely cut off when the signal line S3 becomes in the low level, and the discharge current which has a polarity opposite to the polarity of "V1" flows through the resistors R1 and R2 to the capacitor C1.

Figure 5:
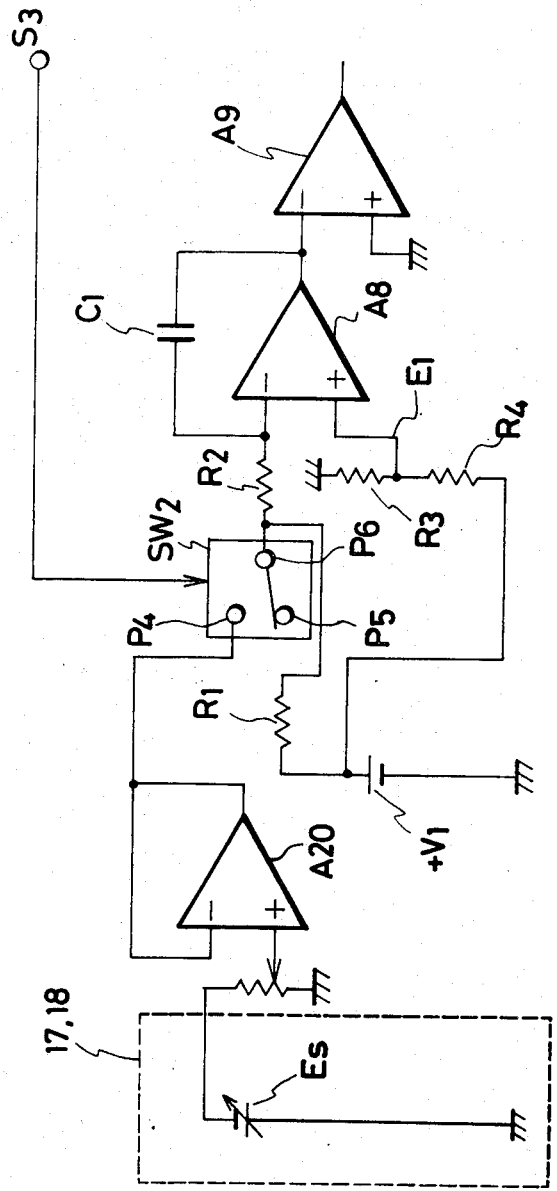
FIG. 5 is a circuit diagram for explaining the operation of an operational amplifier A7 of analog section of analog to digital converter.

An operational amplifier A8 which functions as an integrator receives a voltage E1 divided by the resistors R3 and R4, at the its non-inverting terminal as shown in FIG. 5.

In the case that the terminal $P_3$ of the switch SW1 is connected to the terminal $P_1$, a comparator A9 is used for determining the output of the operational amplifier A8 as a portion of the analog to digital converter but in the case that the terminal $P_3$ of the switch SW1 is connected to the terminal $P_2$, the comparator A9 is used for monitoring the battery voltage. The signal line $S_2$ is connected to the switch SW1 which is controlled by the signal on the signal on the signal line $S_2$.

Referring to the detection circuit 20, the signal voltage of the operational amplifier A6 is applied to the detection circuit 20 and the detection circuit 20 functions as a filter and produces on signal line S4 the reference pulse in synchronism with the pulse pressure.

An operational amplifier A10 consists of a quadratic (second order) band pass filter and a low pass filter.

Referring to the K-sound system, the reference numeral 1 depicts a K-sound microphone of piezoelectric type which produces a relatively loud sound.

The output of the K-sound microphone 1 is amplified to a predetermined voltage level in an amplifier 21.

The amplifier 21 includes a high pass filter 22 to prevent an operational amplifier A12 from saturating, and functions as an impedance matching element.

The noise component contained in the detected K-sounds is eliminated by a quadratic high pass filter 23 and a quadratic low pass filter 24.

The quadratic low pass filter 24 is of the multifeedback type and has amplifying effect and operation. The output of the filter 24 is fed to a comparator A15 which produces digital pulses at its output terminal.

FIG. 5 is a circuit diagram for explaining the function of the operational amplifier A7 of FIG. 4A.

The amplifier A7 performs the function as that of an operational amplifier A20 and a switch SW2 shown in FIG. 5, that is to say, it operates as an electronic switch and a voltage follower to change the charge current of the double integral type analog to digital converter to the discharge current thereof and vice versa and operates as a voltage follower.

When the signal line $S_3$ is in the high level, a terminal $P_6$ of the switch SW2 is connected to a terminal $P_4$ and the input voltage of the operational amplifier A20 is applied to the resistor R2. In other words, the operational amplifier A7 functions as a voltage follower.

Figure 6:
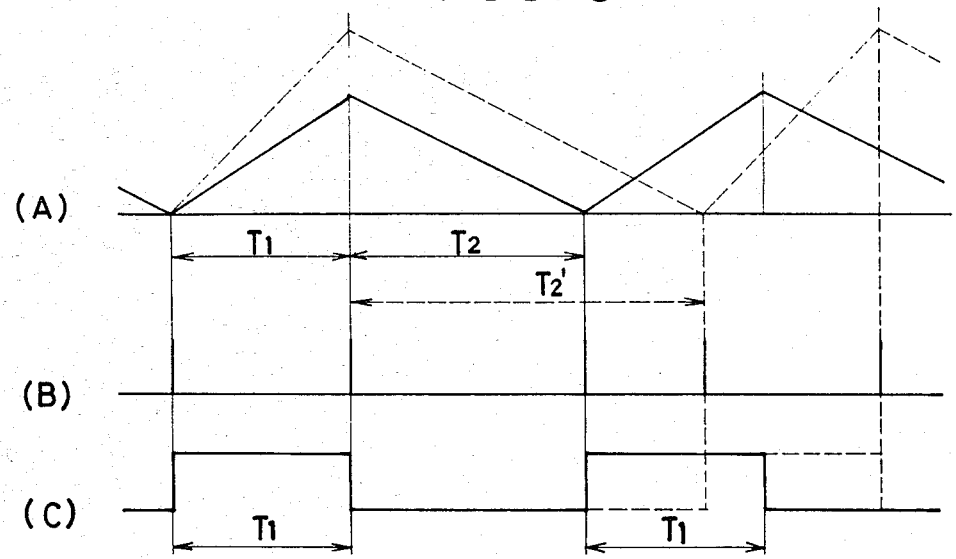
FIG. 6 is time chart showing output waves of the double integral type analog to digital converter.
Figure 7:
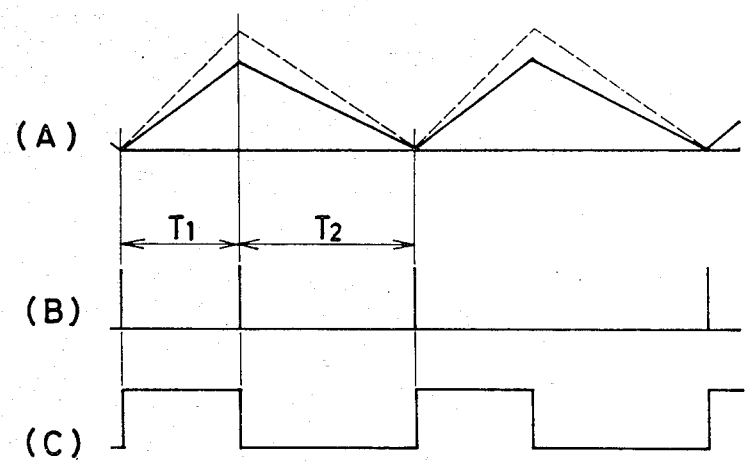
FIG. 7 is another time chart showing output waves of the double integral type analog to digital converter, FIG. 8 are waveforms showing an output of Korotkoff sound and the pressure pulses in case of eliminating a feedback circuit of FIG. 4B.

The capacitor C1 is charged as shown by the up-slope lines in FIGS. 6 and 7 by the charge current which is determined by the input voltage and the resistor R2 at the charge time (T1 of FIGS. 6 and 7), whereas the capacitor C1 is discharged as shown by the down-slope lines in FIGS. 6 and 7 by the discharge current which is determined by the resistors R1, R2 and +V1 at the discharge time (T2 or T'2 of FIGS. 6 and 7).

At the discharge time, the switch SW2 is controlled to connect the terminal P6 to the terminal P5 by making the signal line S3 in the low level. In other words, the operational amplifier A7 is cut off.

FIG. 6 shows time charts showing output waves of the double integral type analog to digital converter.

In FIG. 6, (A) is the output of the operational amplifier A8, (B) is the output of the comparator A9 and (C) is the signal waveform of the signal line S3.

T1 denotes the charge time and T2 the discharge time.

The following equation is obtained because the quantity of the electric charge to flow into the capacitor C1 in the charge time T1 is equal to that of the electric charge to flow out from the capacitor C1 in the discharge time T2.

$$(Es/R2) \cdot T1 = Id \cdot T2 = (+V1/R1+R2) \cdot T2 \quad (1)$$

where Es is a signal voltage which is the output voltage of the operational amplifier A6 and $Id = Er/R1+R2$ is the reference discharge current.

Assuming that the charge time T1 is constant, the signal voltage Es is found by measuring the discharge time T2.

On the other hand, the signal voltage Es is found by the following equation because the pressure sensitivity of the pressure transducer 17 is proportional to the contant current value.

$$Es = K \cdot \alpha \cdot Is \cdot P \quad (2)$$

Where K is the total gain of the operational amplifiers A4–A6, $\alpha$ is the coefficient of pressure sensitivity, P is the pressure value and $Is = (R5/R5+R6) \cdot (+V1/R7)$ is the driving current of the pressure transducer 17.

Accordingly, from the equations (1) and (2), $$T2 = K \cdot \alpha \cdot (R1+R2/R2) \cdot (R5/(R5+R6) \cdot R7) \cdot P \cdot T1$$

The discharge time T2 does not depend on the voltage value +V1 of the reference voltage circuit 15, that is to say, the variation of the reference voltage does not effect the accuracy of the pressure measurement. The dotted line of FIG. 6 shows the output of the operational amplifier A8 when the absolute voltage value of Es in FIG. 5 becomes greater than that of the voltage value Es denoted by the solid line of FIG. 6, that is, when the pressure of the cuff becomes greater, or when the output voltage of the sensor becomes greater by the variation, such as a temperature drift, although the cuff pressure does not become greater.

In FIG. 7, the solid line shows the slope in the case of a non-variation of the reference voltage and the dotted line shows the slope in the case of a variation of the reference voltage.

The pressure transducer 17 increases its current value and the pressure sensitivity thereof becomes higher when the variation value of the reference voltage is greater.

The charge current increases as shown by the dotted line but the reference discharge current increases simultaneously.

As a result, the discharge time T2 does not vary.

The discharge time T2 does not vary, even if $E1 = (R3/R3+R4) \cdot (+V1)$ is applied to the (+) terminal of the operational amplifier A8 as shown in FIG. 5.

In FIG. 7, (A) is the output of the operational amplifier A8, (B) is the output of the comparator A9 and (C) is the signal waveform of the signal line S3.

Figure 8:
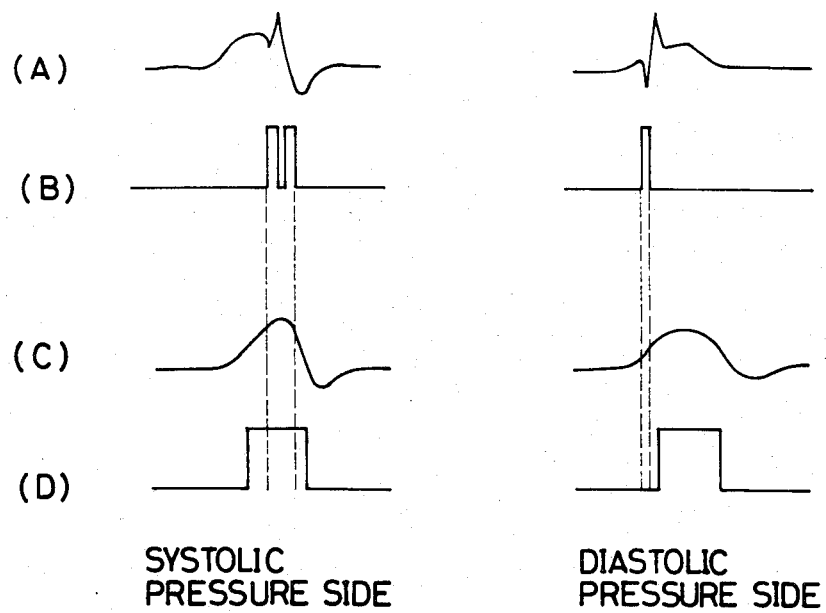

FIG. 8 shows an output of the Korotkoff sound and the waveforms of pressure pulses in case of having removed the feedback circuit consisting of resistor R20 and capacitor C13 shown in FIG. 4B.

(A) is the output of Korotkoff sound and (B) is a Korotkoff sound pulse produced from the comparator A15 serving as a level judgment. (C) is the output of the pressure pulse filter including the operational amplifier A10 and (D) is a pressure pulse which is the output of a comparator A11 serving as a level judgment.

Korotkoff sound is more advanced from the corresponding pressure pulse in the diastolic pressure side than in the systolic pressure side.

In the diastolic pressure side, the Korotkoff sound pulse (B) is not coincident with the pressure pulse (D) as shown in FIG. 8.

However, in FIG. 4B, the detection circuit SD includes the circuit means (feedback circuit) for enlarging the pulse width of the Korotkoff sound pulse.

Figure 9:
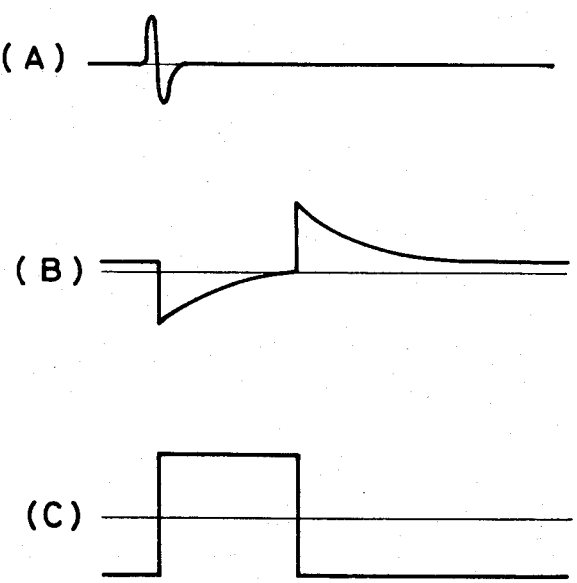
FIG. 9 shows pulse signal waveforms of the detection circuit used in this invention.

In FIG. 4B and FIG. 9, the quadratic low pass filter 24 produces a negative pulse (e) as shown in curve (B) of FIG. 9 when the signal is applied to the K-sound microphone.

The output of the comparator A15 (curve (C) of FIG. 9) goes to the positive side when the output of the quadratic low pass filter 24 exceeds the judgment level determined by the resistors R21 and R22.

The output of the comparator A15 is equal to the output f of the switch circuit.

This output f is applied in a positive feedback fashion through the capacitor C13 and the resistor R20 to the quadratic high pass filter 23.

Accordingly, the output of the quadratic low pass filter 24 becomes negative because the direct current bias of the non-inverting terminal of the operational amplifier A13 is changed when the output f of the comparator A15 becomes positive.

The voltage level at the non-inverting terminal of the comparator A15 goes upward with the time constant determined by the resistors R21, R22 and the capacitor C12.

The output of the comparator A15 recovers its initial state so that it produces at least a one-shot pulse.

The width of the one-shot pulse depends on the resistors R21 and R22, and the capacitor C12 but does not depend on the feedback resistor R20 and the capacitor C13.

In the above mentioned manner, the detection circuit SD is able to produce the appropriate pulse as shown in FIG. 9.

Figure 10:
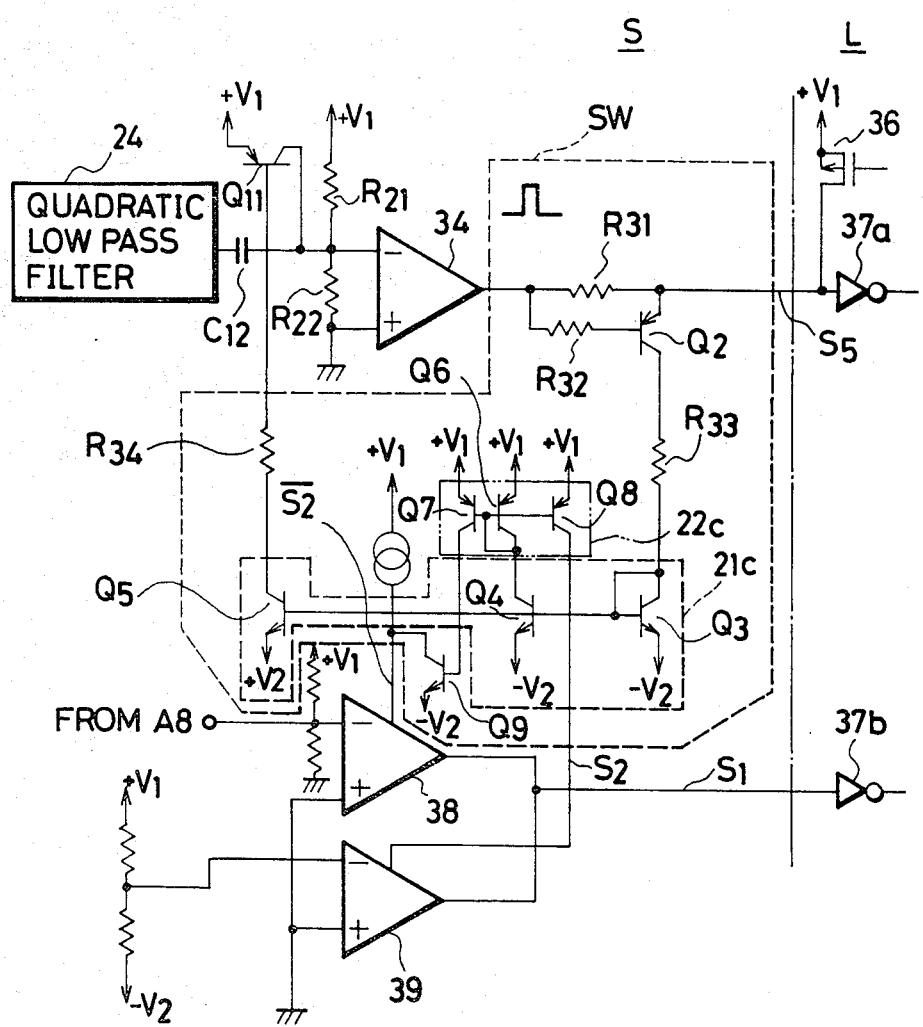
FIG. 10 is a circuit diagram for decreasing the number of signal lines connected between the detection section and the logic section used in this invention.

FIG. 10 is a circuit diagram for decreasing the number of signal lines connected between the detection section S and the logic section L. In this embodiment, the signal line S5 is used as a bidirectional line.

In the blood pressure measurement, a pulse signal is produced at the signal line S5 from a comparator 34 and synchronizes with the K-sound. The comparator 34 and the transistor Q11 are included in the comparator A15 shown in FIG. 4B.

However, of the result of judgment from the battery monitoring circuit 13 appears at the signal line S1 by pulling the signal line S1 up to the power source of the logic circuit L serving as a receiver.

In FIG. 10, the K-sound of the quadratic low pass filter 24 is outputted as a digital pulse from the comparator 34.

When the digital circuit 36 of the logic section L is cut off, the output amplitude of the comparator 34 is transmitted through the resistor R31 and the signal line S5 to Complementary Metal Oxide Semiconductor (C-MOS) element 37a of the arithmetic unit 11 in the logic section.

No voltage drop is produced across a resistor R31 because the current does not flow in the resistor R31 when the C-MOS element is in a high resistance state.

For this reason, a transistor Q2 is off.

Transistors Q3, Q4 and Q5 constitutes a current mirror circuit 21C and transistors Q6, Q7 and Q8 constitute a current mirror circuit 22C.

These current mirror circuits 21C and 22C absorb and flow out the current of the same amplitude as the collector current of the transistors respectively.

The current mirror circuits 21C and 22C do not operate while the transistor Q2 is off.

Accordingly, transistors Q1 and Q9 are off.

Comparators 38 and 39, which are included in the comparator A9 and switch SW1 shown in FIG. 4A, are cut off when the bias current is not applied to them. The signal line S2 cannot provide the bias current to the comparator 39 and the signal line $\overline{S2}$ provides the bias current to the comparator 38.

At the time of the blood pressure measurement, the comparator 38 operates and the comparator 39 is cut off. This state corresponds to the state in which the terminal P3 of the switch SW1 as shown in FIG. 4A is connected to the terminal P1 by the signal on the signal line S2.

The comparator 38 receives the pulse pressure signal through the operational amplifier A8 and the output of the comparator 38 is transmitted to the C-MOS element 37b.

Assuming now that the digital circuit 36 is turned on, that is to say, the signal line S5 is pulled up on the condition that the output of the comparator 34 is in the low level in the normal state.

In this state, the current flows from the digital circuit in the logic circuit section L to the switch Sw in the detection section S in the signal line S5.

The transistor Q2 is turned ON in response to the voltage across the resistor R31 and at the same time the current mirror circuits 21c and 22c operate.

When the current mirror circuits 21c and 22c operate, the transistor Q9 becomes ON and the signal line $\overline{S2}$ cannot provide the bias current signal line S2 provides bias to the comparator 38 but the current from the current mirror circuit 22c to the comparator 39.

The comparator 39 serves as part of the battery monitoring circuit BM of which the judgment result appears on the signal line S1. This state corresponds to the state in which the terminal P3 of the switch SW1 as shown in FIG. 4A is connected to the terminal P2 by the signal on the signal line S2.

When the output of the comparator 34 becomes in the high level, the voltage level at one terminal of the resistor R31 is equal to that at the other terminal thereof so that the transistor Q2 becomes OFF.

For avoiding such a phenomenon, the output of the comparator 34 is maintained at low level by making the transistor Q1 ON.

What is claimed is:

1. In an electronic sphygmonanometer for measuring a person's blood pressure and having detection circuit means for detecting Korotkoff sounds received from a microphone, a pressure transducer for converting a person's blood pressure to an analog electric signal, an amplifier for amplifying the analog electric signal, a detection circuit for detecting a pressure pulse signal based on the amplified analog electric signal and producing a reference pulse signal in synchronism with said pressure pulse signal, a double integral type analog-to-digital converter for converting said analog electric signal to a digital signal, an arithmetic unit for receiving the output signals of said detection circuit means, said detection circuit and said double integral type analog-to-digital converter, and a display device for digitally indicating the person's systolic pressure and diastolic pressure, the improvement comprising: a detection section including said detection circuit means, said pressure transducer, said amplifier, said detection circuit and an analog section of said double integral type analog-to-digital converter; a logic section formed on one MOS IC chip and including a digital section of said double integral type analog-to-digital converter, said arithmetic unit and said digital display device; and a plurality of signal lines connected between said detection section and said logic section and including a first signal line for transmitting said output signal of said detection circuit means to said arithmetic unit, a second signal line for transmitting said reference pulse signal serving as an output of said detection circuit to said arithmetic unit, and a third signal line for transmitting an output of said analog section to said digital section of said double integral type analog-to-digital converter.

2. An electronic sphygmonanometer as claimed in claim 1; wherein said first signal line includes at least one bidirectional signal line, and means for fixing a voltage on said bidirectional signal line to a predetermined voltage in said logic section to change over an electronic switch by flowing current from said logic section to said analog section.

3. An electronic sphygmonanometer as claimed in claim 1; wherein said analog section of said double integral type analog-to-digital converter includes an electronic switch for changing the charge current to discharge current, said electronic switch being comprised of a voltage-follower having a transistor, and an integrator having an integrating capacitor, a first resistor and a second resistor connected in series with said first resistor, one input terminal of said integrator having one of its input terminals thereof connected to said first resistor and the other input terminal thereof connected to a reference voltage.

4. An electronic sphygmonanometer as claimed in claim 1; wherein said detection circuit means includes filter means for eliminating noise, a level judgment circuit for determining the level to detect Korotkoff sounds and connected to said filter means, and feedback means connected between an output of said level judgment circuit and said filter means.

5. An electronic sphygmonanometer as claimed in claim 1; wherein said double integral type analog-to-digital converter includes charging means and discharging means; said discharging means being connected to a reference voltage source in order to control the electric charge quantity in proportion to the reference voltage of said reference voltage source; said charging means being connected to a pressure-to-voltage converting means including said pressure transducer, said pressure-to-voltage converting means being connected to said reference voltage source in order to control the sensitivity of said pressure-to-voltage converting means.

* * * * *